United States Patent [19]

Daly

[11] 4,230,895
[45] Oct. 28, 1980

[54] THERMAL HYDRODEALKYLATION OF ALKYL PHENOLS

[75] Inventor: Francis P. Daly, Lawrenceville, N.J.
[73] Assignee: Hydrocarbon Research, Inc., Lawrenceville, N.J.
[21] Appl. No.: 964,813
[22] Filed: Nov. 30, 1978
[51] Int. Cl.³ ............................................. C07C 37/50
[52] U.S. Cl. .................................. 568/805; 568/806
[58] Field of Search ............................. 568/805, 806

[56] References Cited

U.S. PATENT DOCUMENTS

| | | | |
|---|---|---|---|
| 2,003,941 | 6/1935 | Kahl ...................................... | 568/805 |
| 2,366,497 | 1/1945 | Dawson ................................ | 568/805 |
| 2,786,873 | 3/1957 | Ohsol et al. .......................... | 568/805 |
| 3,284,513 | 11/1966 | Dedinas et al. ...................... | 568/805 |

FOREIGN PATENT DOCUMENTS

| | | | |
|---|---|---|---|
| 786389 | 5/1968 | Canada ................................... | 568/805 |
| 787970 | 6/1968 | Canada ................................... | 568/805 |
| 399498 | 4/1974 | U.S.S.R. ................................. | 568/805 |

OTHER PUBLICATIONS

Well's et al., "I & EC Process Design and Development, " Vol. 1, No. 1, Jan. 1962 Thermal Dealkylation-Hydrocracking of Alkylphenols.

Primary Examiner—Werren B. Lone
Attorney, Agent, or Firm—Michael A. Jacobs

[57] ABSTRACT

The present invention provides a process, for the thermal dealkylation of alkylated phenols, which process comprises reacting a feed solution containing alkylated phenols and gaseous hydrogen in the presence of water vapor, the reaction being carried out at total pressure of 400 to 800 psig, temperature ranging from about 1000° to about 1500° F., and the weight percent water vapor in the reaction being from about 10 to about 40 Wt % of the alkylated phenol feedstock.

11 Claims, No Drawings

THERMAL HYDRODEALKYLATION OF ALKYL PHENOLS

BACKGROUND OF THE INVENTION

1. Field of the Invention

The present invention is related to a process for dealkylating alkyl phenols. More specifically, the present invention is directed to a thermal dealkylation process for alkylated phenols to yield phenol.

2. Description of the Prior Art

The market for phenol is much greater than that for alkylated phenols normally obtained from coal tar or from petroleum or coal hydrogenation. Thus, the production of phenol from alkylated phenols is an area which has received much attention from researchers.

Dealkylation of alkyl phenols by thermal cracking is known in the prior art. However, the prior art methods suffer from the disadvantage that not only does dealkylation occur, but there is also a substantial amount of dehydroxylation so that the less valuable benzene is formed instead of phenol.

It has been proposed to dealkylate an alkylated phenol by reacting hydrogen and the alkylated phenol over a solid catalyst, such as barium oxide, silica gel, nickel sulphide, aluminum oxide, and so forth, for a short period of time. However, in such a process, a large amount of the cresol present in the feed remains unchanged. Furthermore, there is conversion of part of the phenols present to benzene and other hydrocarbons.

Thus, there exists a need for a process whereby the alkyl substituent in an alkylated phenol may be removed without simultaneously removing the hydroxyl group.

It has been discovered by the present inventor that substituent alkyl groups may be removed from alkylated phenols by reacting a feed solution comprising a mixture of alkylphenols with hydrogen in the presence of water vapor, the reaction being conducted at elevated pressures and temperatures. It has been discovered that by hydrodealkylating alkyl phenols in the presence of water vapor, the conversion rate of the alkyl phenols as well as the selectivity for phenol, the desired product, are substantially improved.

SUMMARY OF THE INVENTION

According to the present invention, solution alkylated phenols are dealkylated in the presence of water vapor by reacting the feed solution comprising a mixture of alkylated phenols with hydrogen at a temperature range from about 1000° to 1500° F. at a total reaction pressure of about 400 to about 800 psig. The amount of water vapor present is within the range of from about 10 to about 40% by weight, based on the total weight of the feed solution. By having water vapor present in the reaction, the phenol selectivity may be improved by as much as 20%.

DETAILED DESCRIPTION OF THE INVENTION

The present invention is related to a process for dealkylating alkylated phenols. The present process comprises reacting feed solution comprising a mixture of alkylated phenols with hydrogen in the presence of water vapor and at an elevated temperature and pressure to form the desired phenol.

As suitable feed solution to be treated according to this invention, cresols, xylenols, or other higher phenols, or mixtures thereof, may be used. Water can be either added to the feed solution so as to form an emulsion or pressurized steam can be added separately to the reaction zone. The amount of water which may be present in the reaction ranges from about 10 to about 40% by weight, based on the total weight of the feed solution. The preferred amount of water vapor present is from about 10 to about 20% by weight. For reasons of improved operability, the water vapor present in the reaction zone is preferably provided by steam injection.

In the presence of water vapor, the feed solution is reacted with gaseous hydrogen at a temperature of from about 1000° to about 1500° F., with from about 1100° to about 1300° F. being preferred. The reaction is carried out at a total pressure ranging from about 400 to about 800 psig, although the preferred pressure range is from about 450 to about 650 psig.

The mole ratio of hydrogen to phenols is within the range of from about 2 to about 6, with from about 3.5 to 5.0 being preferred. As to the volume hourly space velocity, this should range from about 0.5 to about 3.0 ml alkylphenol/hour/ml reactor volume, with from about 1.0 to about 2.0 being preferred.

It has been found that by hydrodealkylating the feed solution in the presence of water vapor, the phenol selectivity may be improved by as much as 20%. The apparent reason for this improvement is believed to be a shift in the dehydroxylation equilibrium. The products of thermal hydrodehydroxylation of cresol include toluene and water. By increasing the concentration of water vapor in the reaction zone, the reaction equilibrium is shifted against dehydroxylation. However, the above mechanism merely represents an explanation offered by the present inventor, who does not wish to be bound thereby.

The following example further illustrates the present invention. Since the example is intended for illustrative purposes only, it should not be construed as limiting.

EXAMPLE

A series of experiments were conducted to show the effects of the presence of water vapor in thermal hydrodealkylation of alkyl phenols. The experimental conditions and results are summarized in Table 1.

The data shown in Table 1 clearly indicate that the presence of about 14% by weight of water in the feed led to an increase in the phenol selectivity ranging from about 8 to about 26%.

TABLE 1

| Run No. | 1 | 2 | 3 | 4 |
|---|---|---|---|---|
| Total Pres., psig | 450 | 600 | 600 | 600 |
| $P_{H_2} + P_{organic}$, psig | 450 | 600 | 600 | 508 |
| Temp., °F. | 1150 | 1150 | 1200 | 1200 |
| Residence time, sec. | 33.1 | 44.4 | 28.2 | 23.2 |
| H$_2$/Feed Ratio, molar | 3.72 | 3.80 | 4.29 | 4.58 |
| Space Velocity, $V_{feed}$/Hr/V reactor | 1.04 | 1.02 | 1.41 | 1.61 |
| Feed Comp, Wt % | | | | |
|   Cresols | 73 | 73 | 91.7 | 78.7 |
|   Xylenols | 27 | 27 | 8.3 | 7.1 |
|   H$_2$O | — | — | — | 14.2 |
| Conversion, Wt % of alkyl phenols in feed | 24.6 | 32.2 | 48.1 | 38.4 |
| Product selectivity, Wt % | | | | |
|   Benzene | 5.1 | 6.4 | 12.3 | 8.2 |
|   Toluene | 40.0 | 37.3 | 35.0 | 34.3 |
|   Phenol | 42.1 | 47.6 | 48.8 | 52.9 |
|   Xylenes | 12.8 | 8.7 | 3.9 | 4.6 |

From the above description, it is apparent that the present invention provides a dealkylation process whereby the phenol selectivity is substantially improved. Such improvement may be attained by either adding water or steam to a feed solution comprising a mixture of alkylated phenols and reacting the water/feed mixture with hydrogen at an elevated temperature, or adding steam directly into the reaction zone. The steam may be unsaturated, saturated, or superheated, with superheated steam being preferred.

What is claimed is:

1. A process for thermal dealkylation of alkylated phenols to form a phenol product comprising mixing a feed solution comprising at least one alkylated phenol with hydrogen and reacting the mixture in the presence of added water vapor at a temperature of from about 1000° to about 1500° F., the amount of water vapor used ranging from about 10 to about 40% by weight, based on the total weight of the feed solution.

2. The process of claim 1 wherein the reaction is carried out at a total pressure of from about 400 to about 800 psig.

3. The process of claim 1 wherein the hydrogen to phenol molar ratio is from about 2 to about 6.

4. The process of claim 1 wherein the reaction is carried out at a volume hourly space velocity of from about 0.5 to about 3.0 ml alkyl phenol/hour/ml reactor volume.

5. The process of claim 1 wherein the amount of water used is from 10 to about 20%, the total pressure is from about 450 to about 650 psig, the temperature is from about 1100° to about 1300° F., the volume hourly space velocity is from about 1.0 to about 2.0 ml alkyl phenol/hour/ml reactor volume, and the hydrogen to feed molar ratio is from about 3.5 to about 5.0.

6. The process of claim 1 wherein the amount of water used is about 14%, the total pressure is from about 450 to about 600 psig, the temperature is from about 1150° to about 1200° F., the volume hourly space velocity is from about 1.0 to about 1.6 ml alkyl phenol/hour/ml reactor volume, and the hydrogen to feed molar ratio is from about 3.7 to about 4.6.

7. The process of claim 1 wherein the water vapor present in the reaction zone is provided by injecting pressurized steam directly into said reaction zone.

8. The process of claim 1 wherein the water vapor added to the feed solution is in the form of unsaturated, saturated, or superheated steam.

9. The process of claim 1 wherein the alkylated phenol is selected from the group consisting of cresols, xylenols, and higher phenols.

10. The process of claim 1 wherein the alkylated phenol is contained in coal tar obtained from coal hydrogenation.

11. In a process of thermal hydrodealkylation of alkylated phenols to form a phenal product comprising reacting a feed solution comprising a mixture of alkylated phenols with hydrogen at a temperature of from about 1000° F. to about 1500° F. and a total pressure of from about 400 to about 800 psig, the improvement comprising adding water vaper to the feed solution prior to the reaction with hydrogen the amount of water added being from about 10% to about 40% by weight of the total weight of the water-feed mixture.

* * * * *